(12) United States Patent
Sackstein

(10) Patent No.: US 8,728,810 B2
(45) Date of Patent: *May 20, 2014

(54) METHODS FOR MODIFYING CELL SURFACE GLYCANS

(75) Inventor: Robert Sackstein, Sudbury, MA (US)

(73) Assignee: Robert Sackstein, Sudbury, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/245,136

(22) Filed: Sep. 26, 2011

(65) Prior Publication Data

US 2012/0107924 A1   May 3, 2012

Related U.S. Application Data

(63) Continuation of application No. 11/810,256, filed on Jun. 4, 2007, now Pat. No. 8,084,236.

(60) Provisional application No. 60/810,469, filed on Jun. 2, 2006.

(51) Int. Cl.
*C12N 5/077* (2010.01)
*A61K 35/28* (2006.01)
*C12N 9/10* (2006.01)

(52) U.S. Cl.
CPC ......... *A61K 35/28* (2013.01); *C12N 2506/1369* (2013.01); *C12N 2501/58* (2013.01); *C12N 9/1051* (2013.01)
USPC ............................ 435/372; 435/193; 424/93.7

(58) Field of Classification Search
None
See application file for complete search history.

(56) References Cited

U.S. PATENT DOCUMENTS

| 5,652,343 | A | 7/1997 | Lasky et al. |
| 5,807,732 | A * | 9/1998 | Lowe et al. ............... 435/358 |
| 5,849,898 | A | 12/1998 | Seed et al. |
| 5,942,417 | A | 8/1999 | Ni et al. |
| 6,124,267 | A | 9/2000 | McEver et al. |
| 7,816,500 | B2 | 10/2010 | Sackstein |
| 7,875,585 | B2 | 1/2011 | Sackstein |
| 7,998,740 | B2 | 8/2011 | Sackstein |
| 8,084,236 | B2 | 12/2011 | Sackstein |
| 2003/0040607 | A1 | 2/2003 | Sackstein |
| 2004/0209357 | A1* | 10/2004 | Xia et al. ................... 435/372 |
| 2005/0214283 | A1 | 9/2005 | Sackstein |
| 2006/0003924 | A1 | 1/2006 | Sackstein |
| 2006/0210558 | A1 | 9/2006 | Sackstein |
| 2006/0281708 | A1 | 12/2006 | Sackstein |
| 2007/0174880 | A1 | 7/2007 | Sackstein |
| 2009/0239296 | A1 | 9/2009 | Sackstein |
| 2009/0310668 | A1 | 12/2009 | Sackstein |

(Continued)

FOREIGN PATENT DOCUMENTS

| WO | 9201049 | 1/1992 |
| WO | 9611012 | 4/1996 |

OTHER PUBLICATIONS

Sako, Dianne, et al. "Expression Cloning of a Functional Glycoprotein Ligand for P-Selectin." Dec. 17, 1983. Cell, vol. 75. pp. 1179-1186.

(Continued)

*Primary Examiner* — Manjunath Rao
*Assistant Examiner* — William W Moore
(74) *Attorney, Agent, or Firm* — Bryan Cave LLP

(57) ABSTRACT

Methods and compositions for modifying glycans (e.g., glycans expressed on the surface of live cells or cell particles) are provided herein.

27 Claims, 7 Drawing Sheets

(Sackstein et. al)

(56) References Cited

U.S. PATENT DOCUMENTS

| | | | |
|---|---|---|---|
| 2011/0177040 A1 | 7/2011 | Sackstein | |
| 2011/0189139 A1 | 8/2011 | Sackstein | |
| 2012/0107281 A1* | 5/2012 | Sackstein | 424/93.7 |

OTHER PUBLICATIONS

Sasaki, Katsutoshi, et al. "Expression Cloning of a Novel GalBeta(1-3/1-4)GlcNAc sigma2,3-Sialyltransferase Using Lectin Resistance Selection." The Journal of Biological Chemistry, vol. 268, No. 30. pp. 22782-22787. 1993.

Skolnick, Jeffrey, et al. "From genes to protein structure and function: novel applications of computational approaches in the genomic era." 2000.

Snapp, Karen R., et al. "A Novel P-Selectin Glycoprotein Ligand-1 Monoclonal Antibody Recognizes an Epitope Within the Tyrosine Sulfate Motif of Human PSGL-1 and Blocks Recognition of Both P- and L-Selectin." Jan. 1998. Blood, vol. 91, No. 1. pp. 154-164.

Spertini, Olivier, et al. "P-Selectin Glycoprotein Ligand 1 Is a ligand for L-Selectin on Neutrophils, Monocytes, and CD34+ Hematopoietic Progenitor Cells." Oct. 1996. The Journal of Cell Biology, vol. 135, No. 2. pp. 523-531.

Stamenkovic, Ivan, et al. "The hemotopoietic and epithlial forms of CD44 are distinct polypeptides with different adhesion potentials for hyaluronate-bearing cells." 1991. The EMBO Journal, vol. 10, No. 2. pp. 343-348.

Tu, Lili, et al. "L-Selectin Binds to P-Selectin Glycoprotein Ligand-1 on Leukocytes." 1996. The Journal of Immunology. vol. 157, No. 9. pp. 3995-4004.

Vachino, Gloria, et al. P-selectin Glycoprotein Ligand-1 Is the Major Counter-receptor for P-selectin on Stimulated T Cells and Is Widely Distributed in Non-functional Form on Many Lymphocytic Cells. 1995. The Journal of Biological Chemistry. vol. 270, No. 37. pp. 21966-21974.

Walcheck, Bruce, et al. "Bovine Gamma/Delta T Cells Bind E-Selectin via a Novel Glycoprotein Receptor: First Characterization of a Lymphocyte/E-Selectin Interaction in an Animal Model." Sep. 1993. J. Exp. Med., vol. 178. pp. 853-863.

Zollner, Olaf, et al. "The E-selectin Ligand-1 Is Selectively Activated in Chinese Hamster Ovary Cells by the (1,3)- Fucosyltransgerases IV and VII." 1996. The Journal of Biological Chemistry. vol. 271, No. 51. pp. 33002-33008.

International Searching Authority. "PCT Notification of Transmittal of the International Search Report or the Declaration." Jun. 4, 2003. PCT Application No. PCT/US01/51014.

International Searching Authority. "PCT Notification of Transmittal of the International Search Report and the Written Opinion of the International Searching Authority, or the Declaration." PCT Application No. PCT/US04/37138. Sep. 12, 2005.

SupplementSupplementary Partial EPO Search Report. EP Application No. EPO01988458. Jul. 19, 2004. ary Partial EPO SearchSupplementary Partial EPO Search Report. EP Application No. EPO01988458. Jul. 19, 2004. Report. EP Application No. EPO01988458. Jul. 19, 2004.

Supplementary Partial European Search Report, Application No. EP01988758.4, Date: Aug. 5, 2004.

European Patent Office. "Communication pursuant to Article 96(2)." EP Application No. 01988458.4 Aug. 5, 2004.

European Examination Report, Application No. EP01988758.4, Dec. 4, 2006.

Srivastava, G., et al., 1992, "Enzymatic transfer of a preassembled trisaccharide antigen to cell surfaces using a fucosyltransferase", TheJournal of Biological Chemistry, vol. 267, No. 31, pp. 22356-22361.

Shinoda, K., et al., 1997, "Enzymatic characterization of a human .alpha.1,3-fucosyltransferase Fuc-TVII synthesized in a B cell lymphoma cell line", The Journal of Biological Chemistry, vol. 262, No. 51, pp. 31992-31997.

Takamatsu, Y., et al., 1998, "Dual control by divalent metal cations and mitogenic cytokines of .alpha.4.beta.1 and .alpha.5.beta.1 integrin avidity expressed by human hemopoietic cells", Cell Adhesion and Communication, vol. 5, pp. 349-366.

Chitlaru, T., et al., 1998, "Modulation of circulatory residence of recombinant acetylcholinesterase through biochemical or genetic manipulation of sialylation levels", Biochemical Journal, vol. 336, No. 3, pp. 647-658.

Schrantz, N., et al., 1999, "Manganese induces apoptosis of human B cells: caspase-dependent death blocked by Bcl-2", Cell Death and Differentiation, vol. 6, pp. 445-453.

Grabovsky, V., et al., 2000, "Subsecond induction of .alpha.4 integrin clustering by immobilized chemokines stimulates leukocyte tethering and rolling on endothelial vascular cell adhesion molecule 1 under flow conditions", Journal of ExperimentalMedicine, vol. 192, No. 4, pp. 495-505.

Yeh, J.C., et al., 2001, "Novel sulfated lymphocyte homing receptors and their control by a Corel extension .beta.1,3-N-acetylglucosaminyltransferase", Cell, vol. 105, No. 7, pp. 957-969.

Chigaev, A., et al., 2001, "Real time analysis of the affinity regulation of .alpha.4-integrin",The Journal of Biological Chemistry, vol. 276, No. 52, pp. 48670-48678.

D'Ippolito, G., et al., 2004, "Marrow-isolated adult multilineage inducible (MIAMI) cells, a unique population of postnatal young and old human cells with extensive expansion and differentiation potential",Journal of Cell Science, vol. 117, pp. 2971-2981.

De Bruyn, K. M. T., et al., 2002, "The small GTPase Rap1 is required for Mn2+- and antibody-induced LFA-1- and VLA-4-mediated cell adhesion", The Journal of Biological Chemistry, vol. 277, No. 33, pp. 29468-29476.

Nandi, A., et al., 2004, "Biomolecular complex between rolling and firm adhesion receptors required for cell arrest: CD44 association with VLA-4 in T-cell extravasation", Immunity, vol. 20, pp. 455-465.

Pittenger, M. F., et al., 2004, "Mesenchymal stem cells and their potential as cardiac therapeutics", Circulation Research, vol. 95, pp. 9-20.

Xia, L., et al., 2004, "Surface fucosylation of human cord blood cells augments binding to P-selectin and E-selectin and enhances engraftment in bone marrow", Blood, vol. 104, No. 10, pp. 3091-3096.

Hidalgo, A. et al., "Enforced fucosylation of neonatal CD34+ cells generates selectin ligands that enhance the initial interactions with microvessels but not homing to bone marrow", 2005, Blood, vol. 105, No. 2, pp. 567-575.

Lapidot, T., et al., 2005, "How do stem cells find their way home?", Blood, vol. 106, No. 6, pp. 1901-1910.

Warnock, D., et al., 2005, "In vitro galactosylation of human IgG at 1 kg scale using recombinant galactosyltransferase", Biotechnology and Bioengineering, vol. 92, No. 7, pp. 831-842.

Sackstein, R., 2005, "The lymphocyte homing receptors: gatekeepers of the multistep paradigm", Current Opinion in Hematology, vol. 12, pp. 444-450.

Hodoniczky, J., et al., 2005, "Control of recombinant monoclonal antibody effector functions by Fc N-glycan remodeling in vitro", Biotechnology Progress, vol. 21, No. 6, pp. 1644-1652.

Berg, Ellen L., et al. "The Cutaneous Lymphocyte Antigen Is a Skin Lymphocyte Homing Receptor for the Vascular Lectin Endothelial Cell-Leukocyte Adhesion Molecule 1." Dec. 1991. J. Exp. Med., vol. 174. pp. 1461-1466.

Borges, Eric, et al. "The Binding of T Cell-expressed P-selectin Glycoprotein Ligand-1 to E- and P-selectin Is Differentially Regulated." 1997. The Journal of Biological Chemistry, vol. 272, No. 45. pp. 28786-28792.

Candal, Francisco J. et al. "BMEC-1: A Human Bone Marrow Microvascular Endothelial Cell Line with Primary Cell Characteristics." 1996. Microvascular Research vol. 52, pp. 221-234.

De Luca, Mariagrazia, et al. "A Novel Cobra Venom Metalloproteinase, Mocarhagin, Cleaves a 10-Amino Acid Peptide from the Mature N Terminus of P-selectin Glycoprotein Ligand Receptor, PSGL-1, and Abolishes P-selectin Binding." 1995. The Journal of Biological Chemistry, vol. 270, No. 45. pp. 26734-26737.

Dimitroff, Charles J., et al. "A distinct glycoform of CD44 is an L-selectin ligand on human hematopoietic cells." Dec. 2000. PNAS, vol. 97, No. 25. pp. 13841-13846.

(56) References Cited

OTHER PUBLICATIONS

Dimitroff, Charles J. "Differential L-Selectin Binding Activities of Human Hematopoietic Cell L-Selectin Ligands, HCELL and PSGL-1." 2001. The Journal of Biological Chemistry, vol. 276, No. 50. pp. 47623-47631.
Dimitroff et al. (2001), J. Of Cell Biol., 153: 1277-1286.
Dougherty, Graeme J., et al. "Molecular Cloning of CD44R1 and CD44R2, Two Novel Isoforms of the Human CD44 Lymphocyte 'Homing; Receptor Expressed by Hemopoietic Cells." Jul. 1991. J. Exp. Med., vol. 174. pp. 1-5.
Finger, Erik B. et al. "Adhesion through L-selectin requires a threshold hydrodynamic shear." Jan. 1996. Nature, vol. 379. pp. 266-269.
Fuhlbrigge, Robert C. et al. "Cutaneous lymphocyte antigen is a specialized form of PSGL-1 expressed in skin homing T cells." Oct. 1997. Nature, vol. 389. pp. 978-981.
Girard, Jean-Philippe, et al. "High endothelial venules (HEVs): specialized endothelium for lymphocyte migration." 1995. Immunology Today, vol. 16, No. 9. pp. 449-457.
Goebeler, Matthias. "Migration of highly aggressive melanoma cells on hyaluronic acid is associated with functional changes, increased turnover and shedding of CD44 receptors." 1996. Journal of Cell Science, vol. 109. pp. 1957-1964.
Goelz, Susan. et al. "Differential Expression of an E-selectin Ligand (SLex) by Two Chinese Hamster Ovary Cell Lin s Transfected with the Same )1,3)-Fucosyltransferase Gen (ELFT)." Jan. 1994. The Journal of Biological Chemistry, vol. 269, No. 2. pp. 1033-1040.
Greenburg, Adam W. et al. "Relationship between selectin-mediated rolling of hematopoietic stem and progenitor cells and progression in hematopoietic development." Jan. 2000. American Society of Hermatology, Blood, vol. 95, No. 2. pp. 478-486.
Guyer, Deborah A. et al. "P-Selectin Glycoprotein Ilgand-1 (PSGL-1) Is a Ligand for L-Selectin in Neutrophil Aggregation." Oct. 1996. Blood, vol. 88, No. 7. pp. 2415-2421.
Hale, L. and Haynes, B. "Bromelain Treatment of Human T Cells Removes CD44, CD45RA, E2/MIC2, CD6, CD7, CD8, and Leu 8/LAM1 Surface Molecules and Markedly Enhances CD2-Mediated T Cell Activation." 1992. The Journal of Immunology 149(12): 3809-3816.
Jalkanen, Sirpa T. et al. "A lymphoid cell surface glycoprotein involved in endothelial cell recognition and lymphocyte homing in man." 1986. Eur. J. Immunol., vol. 15. pp. 1195-1202.
Jalkanen, Sirpa et al. "Biochemical Properties of Glycoprotiens Involved in Lymphocyte Recognition of High Endothelial Venules in Man." Sep. 1988. The Journal of Immunology, vol. 141, No. 5. pp. 1615-1623.
Jutila, Mark A., et al. "Cell Surface P- and E-Selection Support Shear-Dependent Rolling of Bovine Gamma/Delta T Cells." 1994. Journal of Immunology, vol. 153. pp. 3917-3928.
Katoh, Shigeki, et al. "Glycosylation of CD44 Negatively Regulates Its Recognition of Hyaluronan." Aug. 1995. J. Exp. Med., vol. 182. pp. 419-429.
Katoh, Shigeki, et al. "Cutting Edge: An Inducible Sialidase Regulates the Hyraluronic Acid Binding Ability of CD44-Bearing Human Monocytes." 1999. Journal of Immunology. pp. 5058-5061.
Kugelman, Lisa C. et al. "The Core Protein of Epican, a Hparan Sulfate Proteoglycan on Keratinocytes, Is an Alternative Form of CD44." 1992. The Journal of Investigative Dermatology, vol. 99, No. 6.
Lawrence, M.B. et al. "Effect of Flow on Polymorphonuclear Leukocyte/Endothelial Cell Adhesion." Nov. 1987. Blood, vol. 70, No. 5, pp. 1284-1290.
Lawrence, Michael B. et al. "Threshold Levels of Fluid Shear Promote Leukocyte Adhesion through Selectins (CD62L,P,E)." Feb. 1997. The Journal of Cell Biology, vol. 136, No. 3. pp. 717-727.
Maiti, Arpita, et al. "TNF-α Induction of CD44-Mediated Leukocyte Adhesion by Sulfation ." Oct. 30, 1998. Science, vol. 282. pp. 941-943.
Ngo, J. Thomas, et al. "Computational Complexity, Protein Structure Prediction, and the Levinthal Paradox." The Protein Folding Problem and Tertiary Structure Prediction. Chapter 14. K. Merz Jr. and S. LeGrand, Editors. Birkhauser Boston. 1994.
Oxley, Susan M. et al. "Detection of L-Selectin Ligand on a Hematopoietic Progenitor Cell Line." Nov. 1994. Blood, vol. 84, No. 10. pp. 3299-3306.
Picker, Louis J., et al. "A Unique Phenotype of Skin-Associated Lymphocytes in Humans." May 1990. American Journal of Pathology, vol. 136. pp. 1053-1068.
Ramos, Carroll, et al. "Functional Characteristics of L-Selectin Ligands on Human Neutrophils and Leukemia Cell Lines: Evidence for Mucinlike Ligand Activity Distinct From P-Selectin Glycoprotein Ligand-1." Feb. 1998. Blood, vol. 91, No. 3. pp. 1067-1075.
Sackstein, Robert, et al. "A hematopoietic cell L-selectin ligand that is distinct from PSGL-1 and displays N-glycan-dependent binding activity." Oct. 2000. Blood, vol. 96, No. 8. pp. 2765-2774.
Sackstein, Robert, et al. "A Hematopoietic Cell L-Selectin Ligand Exhibits Sulfate-Independent Binding Activity." Apr. 1997. Blood, vol. 89, No. 8. pp. 2773-2781.
Sackstein, Robert. "The Bone Marrow is Akin to Skin: HCELL and the Biology of Hematopoietic Stem Cell Homing." May 2004. The Journal of Investigative Dermatology, vol. 122: 5. pp. 1061-1069.

* cited by examiner

Fig. 1 (Sackstein et. al)

Fig. 2 (Sackstein et. al)

Fig. 3 (Sackstein et. al)

Fig. 4 (Sackstein et. al)

Flow Cytometric Analysis of HECA452 Expression on Neural Stem Cells Before and After Fucosyltransferase-VI Treatment
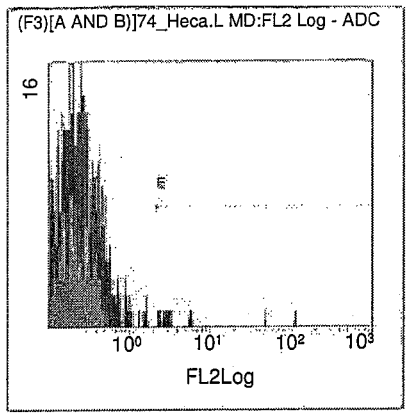
Buffer Rx Neural Stem Cells - HECA452
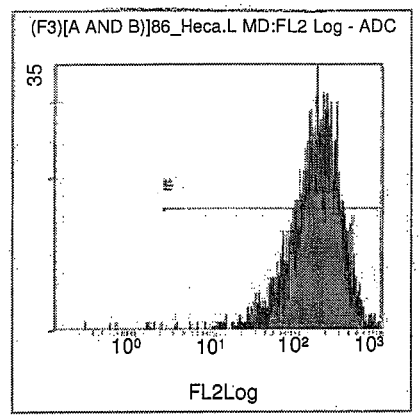
FT6 Rx Neural Stem Cells - HECA452
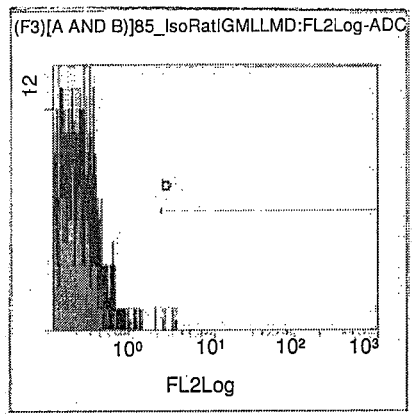
Neural Stem Cells - RtIgM Isotype
Figure 5

Flow Cytometric Analysis of HECA452 Expression on Pulmonary Stem Cells Before and After Fucosyltransferase-VI Treatment
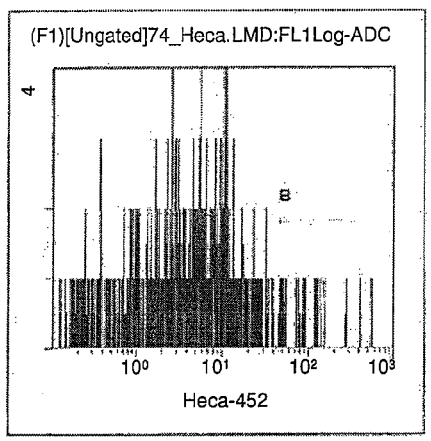
Buffer Rx
Pulmonary Stem
Cells -
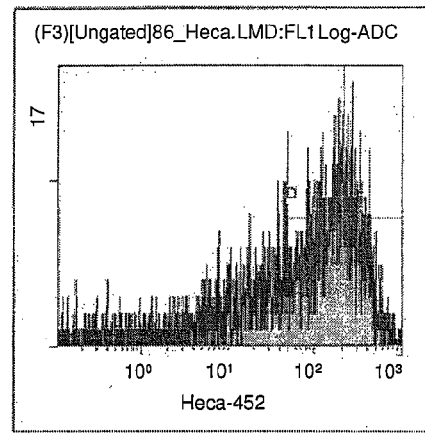
FT6 Rx
Pulmonary Stem
Cells -
HECA452
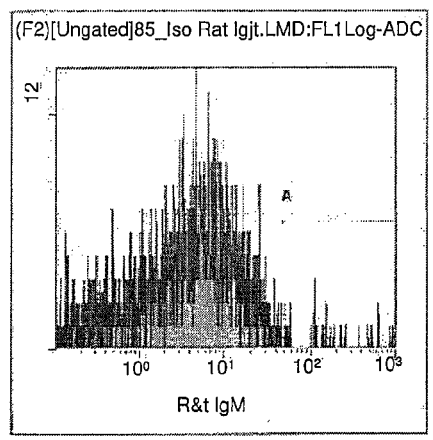
Pulmonary Stem
Cells -
RtIgM Isotype
Figure 6

HECA452 Western Blot of Neural Stem Cells Treated with Fucosyltransferase-VI

US 8,728,810 B2

METHODS FOR MODIFYING CELL SURFACE GLYCANS

RELATED APPLICATIONS

This application is a continuation of U.S. application Ser. No. 11/810,256 filed on Jun. 4, 2007, which claims the benefit of U.S. Ser. No. 60/810,469 filed Jun. 2, 2006, the content of which are incorporated herein by reference in their entireties.

FEDERALLY SPONSORED RESEARCH OR DEVELOPMENT

This invention was made with government support under grants RO1 HL073714 and RO1 HL060528 awarded by National Institutes of Health. The government has certain rights in the invention.

FIELD OF THE INVENTION

This invention relates to compositions and methods for modifying cell-surface glycans on live cells using exogenous glycosyltransferases. Particularly, the composition of methods of the invention preserves the viability and one or more native phenotypic characteristics of the treated cell.

BACKGROUND OF THE INVENTION

The capacity to direct migration of blood-borne cells to a predetermined location ("homing") has profound implications for a variety of physiologic and pathologic processes. Recruitment of circulating cells to a specific anatomic site is initiated by discrete adhesive interactions between cells in flow and vascular endothelium at the target tissue(s). The molecules that mediate these contacts are called "homing receptors", and, as defined historically, these structures pilot tropism of cells in blood to the respective target tissue. At present, only three tissue-specific homing receptors are recognized: L-selectin for peripheral lymph nodes, $\alpha_4\beta_7$ (LPAM-1) for intestines and gut-associated lymphoid tissue, and Cutaneous Lymphocyte Antigen (CLA) for skin (1). Apart from these tissues, it has also been recognized for several decades that circulating cells, especially hematopoietic stem cells, navigate effectively to bone marrow (2). However, extensive investigations on this process over several decades have yielded complex and sometimes conflicting results, providing no direct evidence of a homing receptor uniquely promoting marrow tropism.

From a biophysical perspective, a homing receptor functions as a molecular brake, effecting initial tethering then sustained rolling contacts of cells in blood flow onto the vascular endothelium at velocities below that of the prevailing bloodstream (Step 1) (1). Thereafter, a cascade of events ensue, typically potentiated by chemokines, resulting in activation of integrin adhesiveness (Step 2), firm adherence (Step 3) and endothelial transmigration (Step 4) (3). This "multi-step paradigm" holds that tissue-specific migration is regulated by a discrete combination of homing receptor and chemokine receptor expression on a given circulating cell, allowing for recognition of a pertinent "traffic signal" displayed by the relevant vascular adhesive ligands and chemokines expressed within target endothelium in an organ-specific manner. Following engagement of homing receptor(s) directing trafficking of cells to bone marrow, several lines of evidence indicate that one chemokine in particular, SDF-1, plays an essential role in Step 2-mediated recruitment of cells to this site (2, 4, 5).

The most efficient effectors of Step 1 rolling interactions are the selectins (E-, P- and L-selectin) and their ligands (1). As the name implies, selectins are lectins that bind to specialized carbohydrate determinants, consisting of sialofucosylations containing an $\alpha(2,3)$-linked sialic acid substitution(s) and an $\alpha(1,3)$-linked fucose modification(s) prototypically displayed as the tetrasaccharide sialyl Lewis X (sLe$^x$; Neu5Ac$\alpha$2-3Gal$\beta$1-4-[Fuc$\alpha$1-3]GlcNAc$\beta$1-)) (1, 6). E- and P-selectin are expressed on vascular endothelium (P-selectin also on platelets), and L-selectin is expressed on circulating leukocytes (1). E- and P-selectin are typically inducible endothelial membrane molecules that are prominently expressed only at sites of tissue injury and inflammation. However, the microvasculature of bone marrow constitutively expresses these selectins (5, 7), and in vivo studies have indicated a role for E-selectin in recruitment of circulating cells to marrow (5, 8). Importantly, SDF-1 is constitutively expressed in high concentration within the marrow and is co-localized uniquely with E-selectin on the specialized sinusoidal endothelial beds that recruit blood-borne cells to the bone marrow (5).

Two principal ligands for E-selectin have been identified on human hematopoietic stem/progenitor cells (HSPC), PSGL-1 (9) and a specialized sialofucosylated CD44 glycoform known as Hematopoietic Cell E-/L-selectin Ligand (HCELL) (10, 11). CD44 is a rather ubiquitous cell membrane protein, but the HCELL phenotype is found exclusively on human HSPCs. In contrast to HCELL's restricted distribution, PSGL-1 is widely expressed among hematopoietic progenitors and more mature myeloid and lymphoid cells within the marrow (9). HCELL is operationally defined as CD44 that binds to E-selectin and L-selectin under shear conditions, and is identified by Western blot analysis of cell lysates as a CD44 glycoform reactive with E-selectin-Ig chimera (E-Ig) and with mAb HECA452, which recognizes a sialyl Lewis X-like epitope Like all glycoprotein selectin ligands, HCELL binding to E- and L-selectin is critically dependent on $\alpha(2,3)$-sialic acid and $\alpha(1,3)$-fucose modifications (10-13). On human HSPCs, HCELL displays the pertinent sialofucosylated selectin binding determinants on N-glycans (10, 12). In vitro assays of E- and L-selectin binding under hemodynamic shear stress indicate that HCELL is the most potent ligand for these molecules expressed on any human cell (10, 13). Importantly, though E-selectin is constitutively expressed on microvascular endothelium of the marrow, this molecule is prominently expressed on endothelial beds at all sites of tissue injury (e.g., sites of ischemia-reperfusion injury or trauma) or inflammation.

SUMMARY OF THE INVENTION

The invention features compositions and methods for modifying glycans expressed on the surface of living, e.g. viable cells. The composition and methods allow modification of cell-surface glycans while preserving cell viability and one or more phenotypic characteristics of the cell. For example, the methods and compositions can be employed to modify particular phenotypic characteristics of the cell (such as glycosylation) while preserving one or more other phenotypic characteristics (e.g., mutipotency) of the cell.

In one aspect, the invention features a composition for modifying (ex vivo or in vitro) a glycan, e.g., a glycan expressed on the surface of a cell or a particle or cell fragment (e.g., a mammalian cell or a platelet or a cell membrane-derived substance/fragment such as a liposome. The composition includes a purified glycosyltransferase (e.g., a recombinant glycosyltransferase) and a physiologically acceptable solution, wherein the physiologically acceptable solution is free of one or more divalent metal co-factors (e.g., the solution is free of manganese, magnesium, calcium, zinc, cobalt or nickel). In various embodiments, the glycosyltransferase is a fucosyltransferase (e.g., an alpha 1,3 fucosyltransferase, e.g., an alpha 1,3 fucosyltransferase III, alpha 1,3 fucosyltransferase IV, an alpha 1,3 fucosyltransferase VI, an alpha 1,3 fucosyltransferase VII or an alpha 1,3 fucosyltransferase IX), a galactosyltransferase, or a sialyltransferase.

The composition can include more than one glycosyltransferase and/or may include one or more additional agents, such as a donor substrate (e.g., a sugar). Donor substrates include fucose, galactose, sialic acid, or N-acetyl glucosamine.

The glycosyltransferase has enzymatic activity. Optimally, the glycosyltransferase is capable of transferring 1.0 mmole of sugar per minute at pH 6.5 at 37° C. The composition does not affect integrin adhesion of the cell or cell particle.

The composition can include any physiologically acceptable solution that lacks divalent metal co-factors. In various embodiments, the physiologically acceptable solution is buffered. The physiologically acceptable solution is, e.g. Hank's Balanced Salt Solution, Dulbecco's Modified Eagle Medium, a Good's buffer (see N. E. Good, G. D. Winget, W. Winter, T N. Conolly, S. Izawa and R. M. M. Singh, *Biochemistry* 5, 467 (1966); N. E. Good, S. Izawa, *Methods Enzymol.* 24, 62 (1972) such as a HEPES buffer, a 2-Morpholinoethane-sulfonic acid (MES) buffer, phosphate buffered saline (PBS).

In various embodiments, the physiologically acceptable solution is free of glycerol.

The compositions can be used for modifying a glycan on the surface of a cell such as a stem cell (e.g., a mesenchymal stem cell, a hematopoietic stem cell), a progenitor cell (e.g., a neural stem/progenitor cell or pulmonary stem/progenitor cell) or a cell of hematopoietic lineage (e.g., a leukocyte, a lymphocyte), or a cell particle (e.g., a platelet) or a liposome In another aspect, the invention features a kit for modifying a glycan on the surface of a cell or particle. The kit includes a purified glycosyltransferase, and instructions for contacting a cell with the glycosyltransferase in a physiologically acceptable solution which is free of one or more divalent metal co-factors.

In another aspect, the invention features a method for modifying a glycan on the surface of a cell or particle. The method includes contacting a cell or cell particle with a glycosyltransferase in a physiologically acceptable solution free of divalent metal co-factors under conditions in which the glycosyltransferase has enzymatic activity and the viability of the cell or cell particle population is at least 70%, 80%, 90%. 95%, 97%. 98%, 99% or more. Viability is measures a 2, 4, 6, 8, 12, 24 hours after contact with the glycosyltransferase.

In various embodiments, the cell or particle is contacted with more than one glycosyltransferase and its appropriate donor substrate (e.g. sugar). For example, the cell is contacted with two glycosyltransferases simultaneously, or sequentially, each adding a distinct monosaccharide in appropriate linkage to the (extending) core glycan structure). The method is useful, e.g., for modifying glycans on the surface of cells, e.g. stem cells or differentiated cells or cell particles such as platelets. Cells include for example a mesenchymal cell, hematopoietic stem cells, tissue stem/progenitor cells such as a neural stem cell, a myocyte stem cell, or a pulmonary stem cell, an umbilical cord stem cell, an embryonic stem cell or a leukocyte. The cell or cell particle expresses CD44, e.g., $\alpha(2, 3)$ sialyated CD44. The cell or cell particle does not express CD34 or PSGL-1. After modification the cell or cell particle binds E-selectin and or L-selectin. The modified cell or cell particles do not bind P-selectin In various aspects the methods are useful to increase the affinity of the cells for a ligand, and/or to increase the in vivo engraftment/homing potential of the cells when administered to a subject, to prevent clearance of administered cells or platelets (extend the circulatory half-life), or to alter the ability of a platelet to aggregate or to bind to substrates (e.g., endothelium, leukocytes, extracellular matrix, etc.).

Also included in the invention are the cells or cell particles produced by the methods of the invention.

The invention also features methods of increasing engraftment potential of a cell, treating or alleviating a symptom of an immune disorder, tissue injure or cancer by administering to a subject, e.g. human a composition comprising the cells of the invention.

The details of one or more embodiments of the invention are set forth in the accompanying drawings and the description below. Other features, objects, and advantages of the invention will be apparent from the description and drawings, and from the claims.

Thereafter, CD44 was immunoprecipitated (using anti-CD44 mAb Hermes-1) from equivalent cell lysates of FTVI-treated and untreated cells, and immunoprecipitates were digested with N-glycosidase F(+) or buffer treated (−). Immunoprecipitates were then resolved by reducing SDS-PAGE (4-20% gradient) and blotted with HECA452, E-Ig or another anti-human CD44 mAb (2C5). As shown, N-glycosidase F treatment abrogates HECA452 and E-Ig staining of CD44 from FTVI-treated MSC. Results shown are representative of multiple experiments from MSC derived from several marrow donors.

Figure 3:
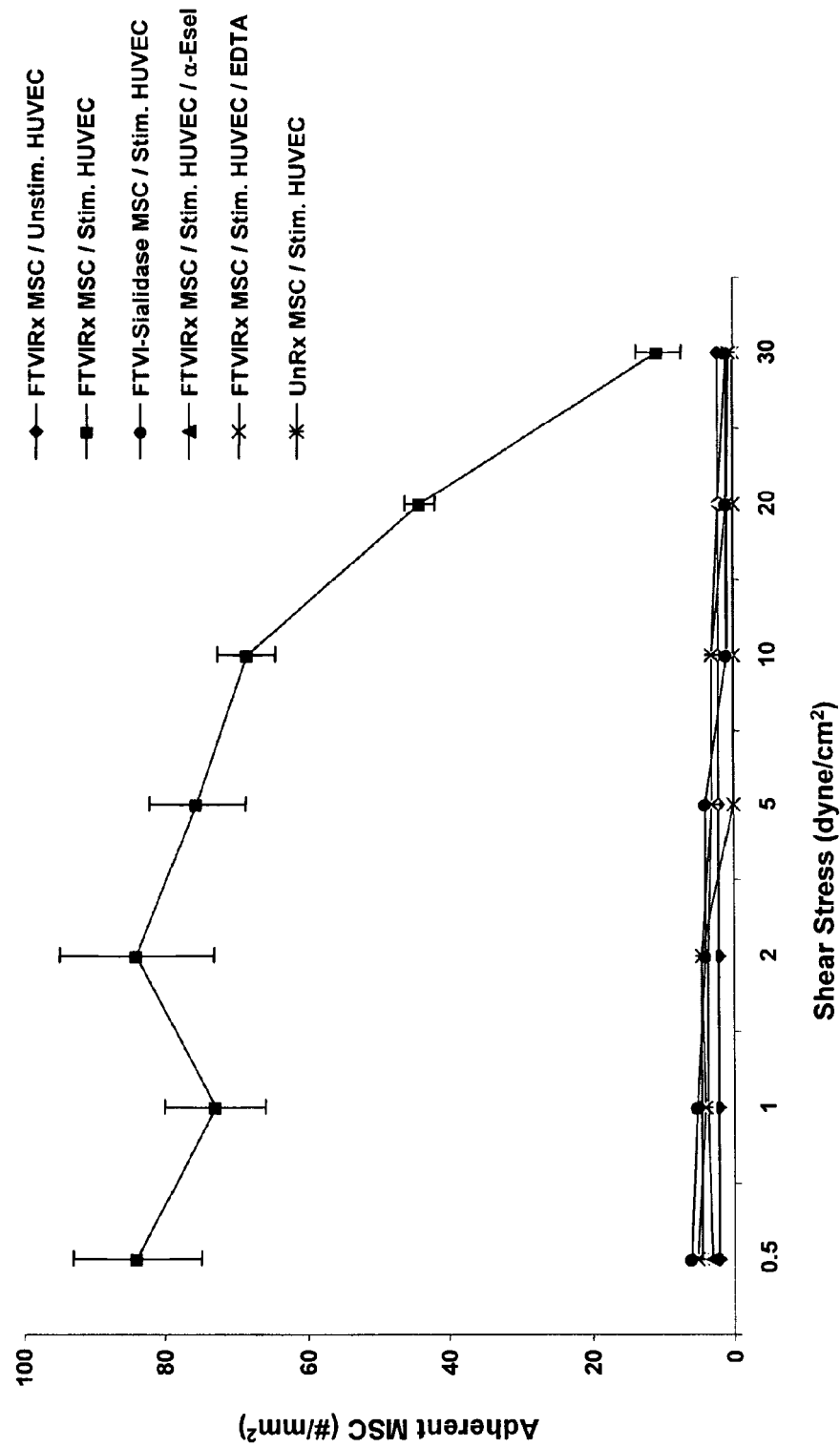

FIG. 3. FTVI-treated human MSC display markedly enhanced shear-resistant adhesive interactions with endothelial E-selectin under defined shear stress conditions. Untreated, FTVI-treated or sialidase digested FTVI-treated MSC were perfused over IL-1β and TNF-α-stimulated human umbilical vein endothelial cells (HUVEC) at 0.5 dyne/cm$^2$. The accumulation of relevant MSC was determined at shear stress of 0.5, 1, 2, 5, 10, 20 and 30 dyne/cm$^2$. In certain instances, EDTA was added to the assay buffer or HUVEC were pretreated with a function blocking mAb to E-selectin prior to use in adhesion assays. Values are means±SEM (n=4 for each group).

Figure 4:
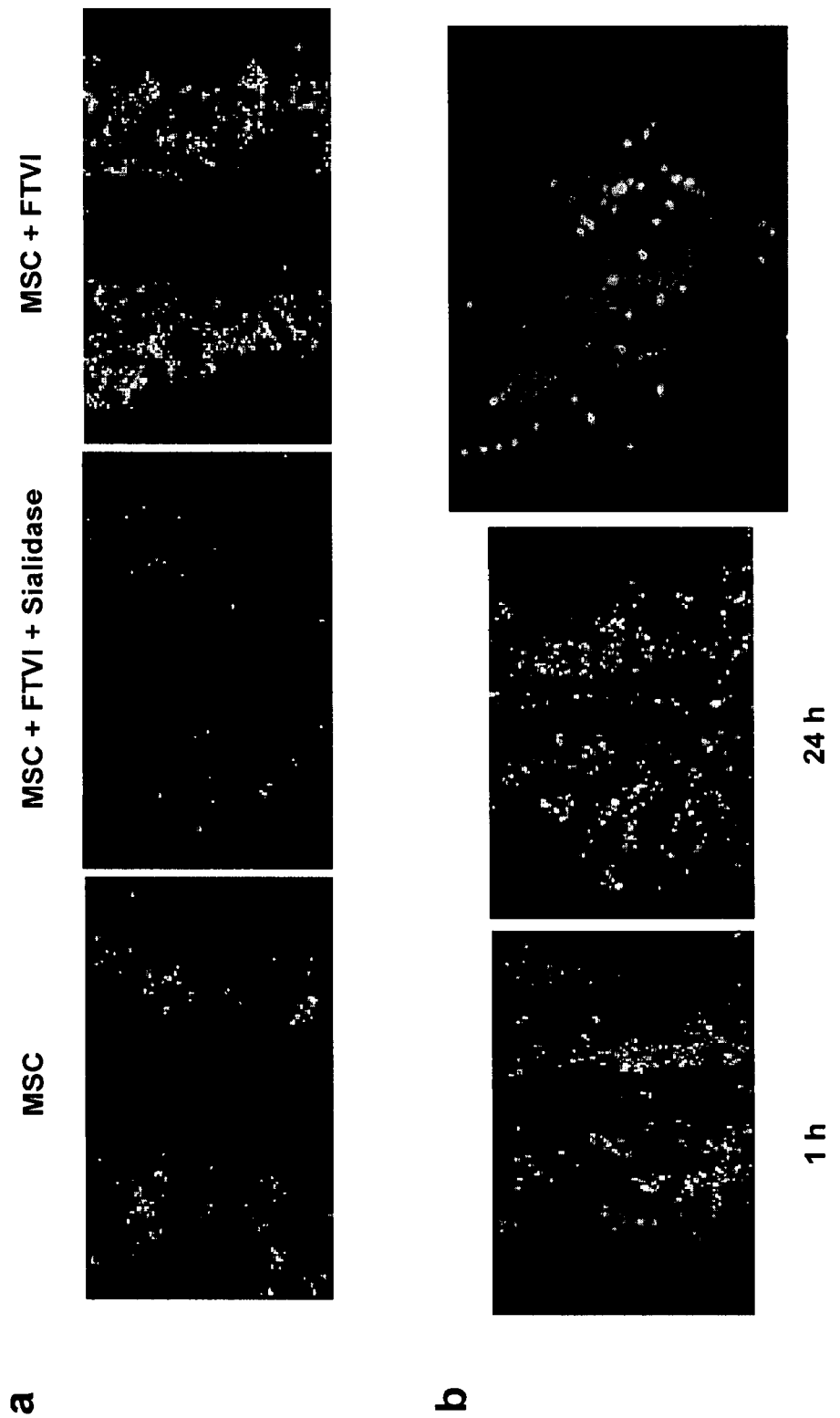

FIG. 4. FTVI-treated, HCELL-expressing human MSC home efficiently to bone marrow in vivo. Montage images of parasagittal region of calvarium assembled from representative experiments of NOD/SCID mice. (a) All images shown in this set of panels were obtained at 1 hour after infusion of relevant cells: Left panel, untreated MSC; Middle panel, FTVI-treated cells digested with sialidase; Right panel, FTVI-treated cells. (b) Results shown are from representative images of one mouse at 1 hour (left panel) and 24 hours (middle panel) after infusion of FTVI-treated MSC. Right panel shows high power color image of sinusoidal perivascular region 24 hours after injection of FTVI-treated MSC, revealing extravascular (parenchymal) infiltrates of infused FTVI-treated MSC: Red speckles are DiD-labeled MSC, green color highlights the sinusoidal vessels, visualized by injection of fluorescent quantum dots (805 nm).

FIG. 5 is a photograph of a Western Blot showing HECA452 reactivity of Neural Stem Cells Treated with Fucosyltransferase-VI FIG. 6 is Flow Cytometric Analysis of HECA452 Expression on Neural Stem Cells Before and After Fucosyltransferase-VI Treatment.

Figure 7:
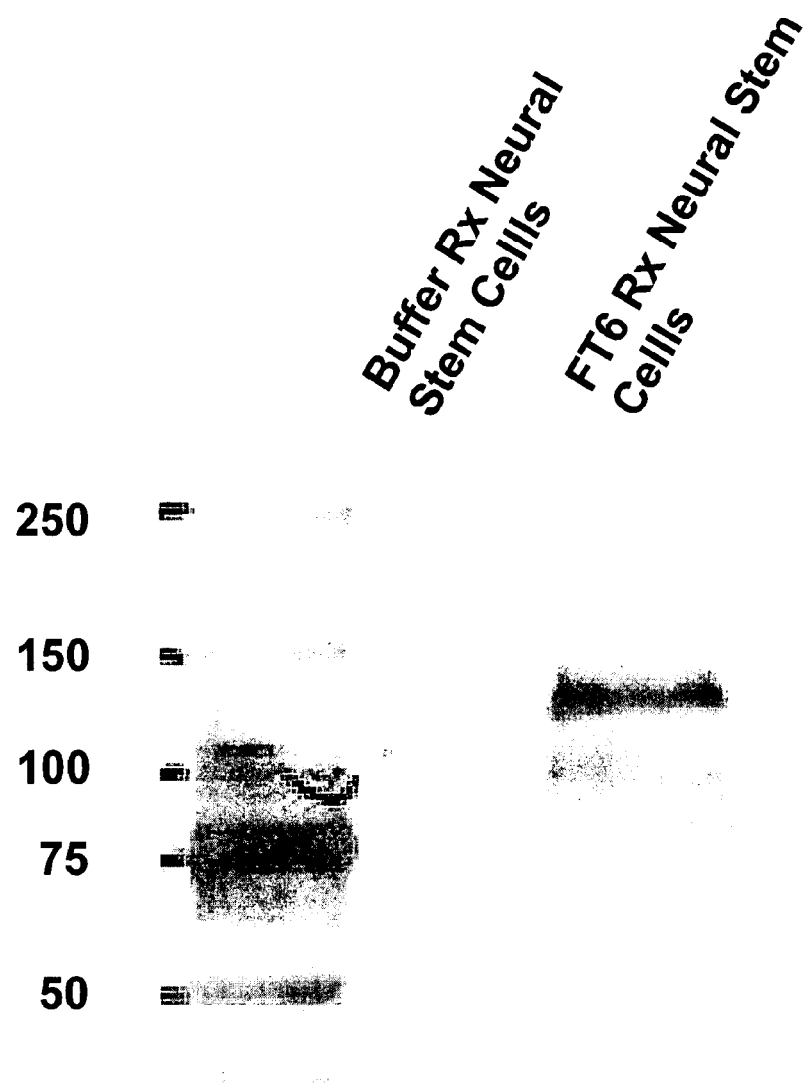

FIG. 7 Flow Cytometric Analysis of HECA452 Expression on Pulmonary Stem Cells Before and After Fucosyltransferase-VI Treatment

DETAILED DESCRIPTION

The invention is based in part on the surprising discovery that glycosyltransferases retain enzymatic activity in the absence of divalent metal co-factors (e.g. divalent cations such as manganese, magnesium, calcium, zinc, cobalt or nickel) and stabilizers such as glycerol. Previously, divalent metal co-factors had been deemed critical for enzymatic activity. The glycosyltransferase compositions according to the invention are particularly useful in modification of glycans on live cells. Previous attempts to modify glycan structures on live cells resulted in cell death and phenotypic changes to the cell due the toxic effects of the metal co-factors and enzyme stabilizers such as glycerol. For ex vivo custom engineering of live cell surface glycans using glycosyltransferases, it is essential that the target cells remain viable and phenotypically conserved following treatment(s). In applications utilizing stem cells, it is also important to analyze whether differentiation along characteristic lineages is affected by enzymatic treatment.

Beyond their recognized effects on cell viability (20), divalent metal co-factors such as Mn$^{++}$ itself triggers signal transduction (21) and activates integrin-adhesiveness (e.g., for VLA-4) at levels well below those employed in forced glycosylation (e.g., fucosylation) (22, 23). These Mn$^{++}$ effects are confounders to the effect(s) of glycosylation on cellular trafficking, as the resulting integrin-mediated firm adhesion would be manifest rampantly at endothelial beds and within tissue parenchyma expressing relevant ligands.

To address these concerns, a new method for high titer fucosyltransferase production in a *Pichia Pastoris* system was developed. Additionally, the fucosyltransferase was stabilized in a buffer (e.g., HBSS) specifically chosen to minimize cell toxicity. Furthermore, enzyme conditions were refined to utilize physiologic buffers in the coupling reaction without input of divalent metal co-factors (e.g., without input of Mn$^{++}$ ions)

These experimental modifications resulted in high efficiency fucosylation of CD44 on MSCs with 100% cell viability following enzymatic treatment. Importantly, kinetic analysis following forced fucosylation showed that cell viability in vitro was retained indefinitely after treatment in all MSC, yet HCELL expression was transient: HCELL levels were stable for 24 hours and declined steadily thereafter to baseline (no HCELL) by 96 hours, presumably reflecting cell turnover of membrane CD44. Importantly, there was no effect on MSC differentiation into various lineages following FTVI treatments, assayed daily for up to 2 weeks following treatment. Thus, FTVI treatment had no apparent effect on the phenotype of MSC, with exception only of HCELL expression (FIG. 2c). In contrast, FTVI treatment of MSC from commercial available FTVI (e.g., compositions containing Mn$^{++}$ and glycerol; Calbiochem) while enhancing HCELL expression cell viability was compromised following these FTVI treatments, with >95% of cells dying within 8 hours of modification. This loss of viability was attributed to exposure to stabilizers (e.g., glycerol) in the commercial enzyme formulations and to exposure to high levels of Mn$^{++}$ (10 mM) used in the enzymatic reaction. Accordingly, the compositions of the invention now make it feasible to ex-vivo engineer glycans on a surface of a viable cell to produce a therapeutic product that is suitable for in vivo administration to a human.

Following forced fucosylation, and despite absence of surface CXCR4 expression, intravenously infused MSC homed robustly to bone marrow, a tissue constitutively expressing vascular E-selectin. These findings establish HCELL as a human bone marrow homing receptor, provide direct evidence that CXCR4 engagement is not obligatory for marrow trafficking, and present new perspectives on the multi-step paradigm.

The finding that enforced HCELL expression confers marrow tropism, and that its functional inactivation by sialidase treatment specifically reverses this effect, defines this CD44 glycoform as a "bone marrow homing receptor". As such, the ability to custom-modify HCELL expression ex vivo may be useful for improving engraftment of HSPCs in clinical transplantation, or for use of MSC in cell-based therapy (e.g., for bone diseases). More generally, the data suggest that enforcing cellular HCELL expression may promote systemic delivery to tissues whose endothelial beds express E-selectin. The high specificity and efficiency of this rather subtle fucose modification of α(2,3)-sialylated-glycoforms of CD44 thus provides guiding principles and technologies for strategies to selectively upregulate HCELL expression for adoptive cellular therapeutics. The facility with which this can be accomplished suggests that rapid translation of this approach to patients should be straightforward. Because E-selectin is displayed prominently at sites of inflammation and ischemia in affected tissues of primates (29, 30), modulation of HCELL expression could lead to directed migration and infiltration of progenitor/stem cells at injured/damaged tissue(s) for regenerative therapeutics. Beyond implications in stem cell-based therapies, these findings also testing of how upregulated E-selectin ligand activity on other cells, such as immunologic effector and regulatory cells, may be harnessed to achieve targeted cell migration in a variety of physiologic and pathologic processes, including immune diseases, infectious diseases, and cancer therapeutics.

Compositions

The invention provides compositions for ex vivo modification of cell surface glycans on a viable cell or cell particle. The compositions include a purified glycosyltransferase polypeptide and a physiologically acceptable solution free of divalent metal co-factors. The composition is free of stabilizer compounds such as for example, glycerol. Glycosyltransferase include for example, fucosyltransferase, galactosyltransferase, sialytransferase and N-acetylglucosaminotransferase. The fucosyltransferase is an alpha 1,3 fucosyltransferase such as an alpha 1,3 fucosyltransferase III, alpha 1,3 fucosyltransferase IV, an alpha 1,3 fucosyltransferase VI, an alpha 1,3 fucosyltransferase VII or an alpha 1,3 fucosyltransferase IX)

Optionally, the composition further includes a sugar donor suitable for the specific glycosyltransferase. For example, when the glycoslytransferase is a fucosyltransferase, the donor is GDP-fucose. Whereas, when the glycosyltransferase is a siayltransferase, the donor is CMP-sialic acid. One skilled in the art would recognize suitable sugar donors.

The glycosyltransferases are biologically active. By biologically active is meant that the glycosyltransferases are capable of transferring a sugar molecule from a donor to acceptor. For example, the glycosyltransferase is capable of transferring 0.1, 0.2, 0.3, 0.4, 0.5, 1.0, 1.5, 2.0, 2.5, 5, 10 or more µmoles of sugar per minute at pH 6.5 at 37° C.

Physiologically acceptable solution is any solution that does not cause cell damage, e.g. death. For example, the viability of the cell or cell particle is at least 80%, 85%, 90%, 95%, 96%, 97%, 98%, 99% or more after treatment with the compositions of the invention. Suitable physiologically acceptable solutions include for example, Hank's Balanced Salt Solution (HBSS), Dulbecco's Modified Eagle Medium (DMEM), a Good's buffer (see N. E. Good, G. D. Winget, W. Winter, T N. Conolly, S. Izawa and R. M. M. Singh, *Biochemistry* 5, 467 (1966); N. E. Good, S. Izawa, *Methods Enzymol.* 24, 62 (1972) such as a HEPES buffer, a 2-Morpholinoethanesulfonic acid (MES) buffer, or phosphate buffered saline (PBS).

Therapeutic Methods

The compositions of the invention, due to their low toxicity on viable cells and high enzymatic activity are useful for the ex vivo or in vitro modification of glycan on the surface of cells or cell particles. Moreover, the modified cells and particles produced using the compositions and methods of the invention are useful in therapeutic settings to achieve targeted cell migration in a variety of physiologic and pathologic processes, including bone disease, immune diseases, infectious diseases, and cancer therapeutics. The Federal Drug Administration imposes (FDA) imposes rigid requirements on all final cell products for human administration. Specifically, the FDA requires a minimum cell viability of 70%, and any process should consistently exceed this minimum requirement. Unlike previous described methods of ex vivo or in vitro modification of glycan on the surface of cells which utilized glycosyltransferases compositions, containing divalent metal co-factors and stabilizers such as glycerol (which resulted in significant cell death), the methods described herein produce a cell based product that meets or exceeds the FDA requirements.

More specifically, the glycan engineering of the cell surface will drive homing of cells to any site where E-selectin is expressed. In particular, since CD44 is a ubiquitously expressed cell membrane protein and is displayed on stem/progenitor cell populations of both "adult" and embryonic types, the capacity to modify glycosylation of this protein by ex vivo glycan engineering to create the HCELL (CD44 glycoform) phenotype will drive migration of intravascularly injected (adoptively transferred) cells in vivo to marrow or to any tissue/organ site where E-selectin is expressed.

Glycans are modified on the surface of a cell or cell particle (e.g. platelet or liposome) by contacting a population of cells with one or more glycosyltransferase compositions according to the invention. The cells are contacted with the glycosyltransferase composition under conditions in which the glycosyltransferase has enzymatic activity. Glycan modification according to the invention results in cells that have at least 80%, 85%, 90%, 95%, 96%, 97%, 98%, 99% or more viability. Viability is determined by methods known in the art such as trypan blue exclusion. Viability is measured 1 hr, 2 hr, 4 hr, 18 hr, 12 hr 24 hr or more after treatment. The phenotype of the cells (other than the glycan modification) is preserved after treatment. By preserved phenotype it is meant the cell maintains its native function and or activity. For example, if the cell is a stem cell it retains its pluripotency.

After modification, the cell or cell particle binds E-selectin and or L-selectin. In various aspects, the modified cell does not bind P-selectin. Preferably, after modification the cells express the sialofucosylated CD44 glycoform known as Hematopoietic Cell E-/L-selectin Ligand (HCELL). After modification, the cell or cell particle is capable of homing in-vivo to the bone marrow and or sites of ischemia or inflammation.

The cell or cell particle is any cell in which cell surface glycan modification is desired. The cell is a stem cell (i.e., multipotent) or a differentiated cell. Stem cells include for example a hematopoietic stem cell, a mesechymal stem cell, a tissue stem/progenitor cell (e.g., a neural stem cell, myocyte stem cell or pulmonary stem cell), an umbilical cord stem cell, or an embryonic stem cell. Differentiated cells includes hematopoietic-lineage cells such as a leukocyte, e.g., a lymphocyte. The lymphocyte can be a B-lymphocyte or T-lymphocyte, or a subset of T lymphocytes, e.g., a "regulatory" lymphocyte (CD4$^+$/CD25$^+$/FOXP3$^+$).

The cell or cell particle expresses CD44. The CD44 is not sialofucosylated. Alternatively the CD44 is alpha (2,3)-sialylated and lacks relevant fucosylations rendering the HCELL phenotype. Enforced glycosylation of CD44 to render HCELL is useful in improving engraftment of hematopoietic stem/progenitor cells (HSPCs) in clinical hematopoietic stem cell transplantation, or for use of MSC in cell-based therapy (e.g., for bone diseases). More generally, the data suggest that enforcing cellular HCELL expression may promote systemic delivery of HCELL-bearing cells to tissues whose endothelial beds express E-selectin.

In various aspects cell does not express PSGL-1, CD34 or both.

The modified cells of the invention because of their increased homing capabilities are useful for example in for improving engraftment of HSPCs in clinical transplantation, for use of MSC in cell-based therapy (e.g., for bone diseases)

or directing migration and infiltration of progenitor/stem cells at injured/damaged tissue(s) for regenerative therapeutics.

For example, the composition are useful for treating a variety of diseases and disorders such as ischemic conditions (e.g., limb ischemia, congestive heart failure, cardiac ischemia, kidney ischemia and ESRD, stroke, and ischemia of the eye), conditions requiring organ or tissue regeneration (e.g., regeneration of liver, pancreas, lung, salivary gland, blood vessel, bone, skin, cartilage, tendon, ligament, brain, hair, kidney, muscle, cardiac muscle, nerve, and limb), inflammatory diseases (e.g., heart disease, diabetes, spinal cord injury, rheumatoid arthritis, osteo-arthritis, inflammation due to hip replacement or revision, Crohn's disease, and graft versus host disease) auto-immune diseases (e.g., type 1 diabetes, psoriasis, systemic lupus, and multiple sclerosis), a degenerative disease, a congenital disease hematologic disorders such as anemia, neutropenia, thrombicytosis, myeloproliferative disorders or hematologic neoplasms and cancer such as leukemia.

Diseases and disorders are treated or a symptom is alleviated by administering to a subject in need thereof a cell composition produced by the methods of the invention. The cell compositions are administered allogeneically or autogeneically.

Example 1

General Methods

Reagents: The following antibodies were from BD Pharmingen: function blocking murine anti-human E-selectin (68-5411; $IgG_1$), rat anti-human CLA (HECA-452; IgM), murine anti-human PSGL-1 (KPL-1; $IgG_1$), purified and FITC-conjugated murine anti-human L-selectin (DREG-56; $IgG_1$), murine anti-human CXCR4 (12G5; $IgG_{2a}$), FITC-conjugated murine anti-human CD18 (L130; $IgG_1$), murine anti-human CD29 (MAR4; $IgG_1$), PE-conjugated murine anti-human CD49d (9F10; $IgG_1$), mouse $IgG_1,\kappa$ isotype, mouse $IgG_{2a}$ isotype, mouse IgM isotype, rat IgG isotype and rat IgM isotype. Rat anti-human CD44 (Hermes-1; $IgG_{2a}$) was a gift of Dr. Brenda Sandmaier (Fred Hutchinson Cancer Research Center; Seattle, Wash.). Recombinant murine E-selectin/human Ig chimera (E-Ig) and murine anti-human CD44 (2C5; $IgG_{2a}$) were from R&D Systems. Murine anti-human $sLe^x$ (KM93; IgM) was from Calbiochem. FITC-conjugated murine anti-human CD11a (25.3; $IgG_1$), PE-conjugated mouse $IgG_1,\kappa$ isotype and FITC-conjugated mouse IgM isotype were from Coulter-Immunotech. FITC-conjugated goat anti-rat IgM, FITC-conjugated goat anti-mouse IgG, FITC-conjugated goat anti-mouse IgM, PE-conjugated strepavidin, alkaline phosphatase (AP)-conjugated anti-rat IgM, anti-mouse Ig, and anti-human Ig were from Southern Biotechnology Associates. *V. Cholerae* sialidase was from Roche.

Human cells: Bone marrow (BM) cells were obtained from harvest filters of healthy individuals donating bone marrow for hematopoietic stem cell transplantation at the Brigham & Women's Hospital/Dana Farber Cancer Institute and Massachusetts General Hospital. BM mononuclear cells (BM-MNCs) were collected by Ficoll-Paque density gradient centrifugation. Human cells were used in accordance with the protocols approved by the Human Experimentation and Ethics Committees of Partners Cancer Care Institutions [Massachusetts General Hospital, Brigham & Women's Hospital and Dana Farber Cancer Institute (Boston, Mass.)]. Human umbilical vein endothelial cells (HUVEC) were obtained from the tissue culture core facility at Brigham & Women's Hospital's Pathology Department and were maintained in M199 supplemented with 15% FBS, 5 units/ml heparin, 50 µg/ml endothelial growth factor and 1% penicillin/streptomycin. To stimulate expression of E-selectin, confluent monolayers of HUVEC were pre-treated with 1 ng/ml IL-1β (Research Diagnostics, Inc; Concord, Mass.) and 10 ng/ml TNF-α (Research Diagnostics, Inc.) for 4-6 hrs prior to use in the adhesion studies.

MSC culture: MSC were maintained in a humidified incubator at 37° C. in an atmosphere of 95% air, 5% $CO_2$ (as per (15)) or in 3% $O_2$, 5% $CO_2$, 92% $N_2$ (as per (16), "MIAMI" cells). For culture of either type of MSC, BMMNCs were plated initially at a density of $2\times10^5/cm^2$ in DMEM-low glucose medium supplemented with 10% fetal bovine serum (FBS) from selected lots. After several days, non-adherent cells were removed and adherent cells were harvested by treatment with 0.05% trypsin/0.5 mM EDTA/HBSS (Invitrogen Corp.) and replated at a density of 50 cells/$cm^2$. Medium was replaced at 48 to 72 hours and every third or fourth day thereafter. Cells were replated when density approached 40% confluence. For all experiments, MSC were used within the first 3 passages, and harvested by treatment with 0.05% trypsin/0.5 mM EDTA/HBSS for less than 3 minutes at 37° C.

Generation of SACK-1 mAb: HCELL was isolated from KG1a cells by immunoaffinity chromatography of cell lysates using anti-CD44 mAb. BALB/c mice were injected with pure HCELL in complete Freund's adjuvant (1:1 emulsion), splitting inoculum 50:50 between skin and intraperitoneal sites. Boosting was performed 2 weeks later with pure HCELL, diluted 1:1 in incomplete Freund's adjuvant and injected intraperitoneally. 10-14 days later, mice were boosted by IV injection of 5 µg HCELL, then spleens were harvested 3 days following IV boost. Splenocytes were fused with NSO myeloma cells. Screening of hybridoma supernatants was initially performed by flow cytometry, against hematopoietic cell lines KG1a (CD44+/HCELL+/HECA452+), HL60 (CD44+/HCELL−/HECA452+), RPMI8402 (CD44+/HCELL−/HECA452−), JURKAT and K562 (both of which are CD44−/HCELL−/HECA452−). SACK-1 mAb was identified as "CD44-specific, carbohydrate-specific", by reactivity to KG1a but not to CD44-cell lines, in conjunction with Western blot evidence of monospecificity for CD44 expressed on KG1a cells, sensitive to digestion with N-glycosidase F (New England Biolabs; N-glycoidase F digestion performed as previously described (10, 12)).

Flow cytometry: Aliquots of cells ($2\times10^5$ cells) were washed with PBS/2% FBS and incubated with primary mAbs or with isotype control mAbs (either unconjugated or fluorochrome conjugated). The cells were washed in PBS/2% FBS and, for indirect immunofluorescence, incubated with appropriate secondary fluorochrome-conjugated anti-isotype antibodies. After washing cells, FITC or PE fluorescence intensity was determined using a Cytomics FC 500 MPL flow cytometer (Beckman Coulter Inc., Fullerton, Calif.).

Recombinant expression and formulation of human α(1,3)-fucosyltransferase VI: *Pichia pastoris* KM 71 (arg4his4aox1: ARG4) host strain containing the human α(1,3)-fucosyltransferase VI (FTVI) gene and the N-terminal signal sequence of *S. cerevisiae* α-factor were used for stable expression and secretion of highly active α(1,3)-fucosyltransferase VI into the medium using online methanol sensing (sterilizable methanol sensor by Raven Biotech, Vancouver, Canada) and regulation of methanol addition by Alitea-pumps (Alitea A. B., Stockholm, Sweden). After the end of fermentation, the broth was cooled down to 10° C. and the *Pichia* cells were separated by a Pellicon-microfiltration system with 0.2 µm membranes and, subsequently, the final formulation was achieved by buffer exchange with HBSS using a Pellicon-ultrafiltration system with 10 kD-UF-membranes (regenerated cellulose).

Recombinant expression and formulation of human sialytransferase: Pichia pastoris KM 71 (arg4his4aox1:ARG4) host strain containing the human sialytransferase gene and the N-terminal signal sequence of S. cerevisiae α-factor were used for stable expression and secretion of highly active sialytransferase into the medium using online methanol sensing (sterilizable methanol sensor by Raven Biotech, Vancouver, Canada) and regulation of methanol addition by Alitea-pumps (Alitea A. B., Stockholm, Sweden). After the end of fermentation, the broth was cooled down to 10° C. and the Pichia cells were separated by a Pellicon-microfiltration system with 0.2 μm membranes and, subsequently, the final formulation was achieved by buffer exchange with HBSS using a Pellicon-ultrafiltration system with 10 kD-UF-membranes (regenerated cellulose).

Recombinant expression and formulation of human glycosytransferase: Pichia pastoris KM 71 (arg4his4aox1:ARG4) host strain containing the human glycosytransferase gene and the N-terminal signal sequence of S. cerevisiae α-factor is used for stable expression and secretion of highly active glycosytransferase into the medium using online methanol sensing (sterilizable methanol sensor by Raven Biotech, Vancouver, Canada) and regulation of methanol addition by Alitea-pumps (Alitea A. B., Stockholm, Sweden). After the end of fermentation, the broth is cooled down to 10° C. and the Pichia cells were separated by a Pellicon-microfiltration system with 0.2 μm membranes and, subsequently, the final formulation is achieved by buffer exchange with HBSS using a Pellicon-ultrafiltration system with 10 kD-UF-membranes (regenerated cellulose).

Recombinant expression and formulation of human N-acetylglucosaminotransferase: Pichia pastoris KM 71 (arg4his4aox1:ARG4) host strain containing the human N-acetylglucosaminotransferase gene and the N-terminal signal sequence of S. cerevisiae α-factor is used for stable expression and secretion of highly active N-acetylglucosaminotransferase into the medium using online methanol sensing (sterilizable methanol sensor by Raven Biotech, Vancouver, Canada) and regulation of methanol addition by Alitea-pumps (Alitea A. B., Stockholm, Sweden). After the end of fermentation, the broth is cooled down to 10° C. and the Pichia cells are separated by a Pellicon-microfiltration system with 0.2 μm membranes and, subsequently, the final formulation is achieved by buffer exchange with HBSS using a Pellicon-ultrafiltration system with 10 kD-UF-membranes (regenerated cellulose).

FTVI and Sialidase treatment: MSC either in confluent monolayer or in suspension were treated with 60 mU/mL FTVI in HBSS containing 20 mM HEPES, 0.1% human serum albumin and 1 mM guanosine diphosphate (GDP)-fucose for 40 min. at 37° C. After the incubation, MSC were washed with HBSS containing 0.2% BSA and 20 mM HEPES. Untreated and FTVI-treated MSC were then used for experiments. In some experiments, MSC were first treated with FTVI and then subjected to sialidase treatment (100 mU/ml V. Cholerae Sialidase, 1 hour, 37° C.) ("FTVI-Sialidase MSC"). Efficacy of sialidase treatment was confirmed in each case by loss of reactivity to KM93 and HECA452 by flow cytometry.

Sialytransferase treatment: Cells are treated with 60 mU/mL of N-sialytransferase, 1 mM CMP-sialic acid or treated with buffer alone (HBSS, 0.1% human serum albumin) for 1 hour at 37° C. After the incubation, the cells are washed with HBSS containing 0.2% BSA and 20 mM HEPES.

Galactosyltransferase treatment: Cells are treated with 60 mU/mL of Galactosyltransferas, 1 mM UDP-galactose or treated with buffer alone (HBSS, 0.1% human serum albumin) for 1 hour at 37° C. After the incubation, the cells are washed with HBSS containing 0.2% BSA and 20 mM HEPES.

N-acetylglucosaminotransferase treatment: Cells are treated with 60 mU/mL of N-acetylglucosaminotransferase, 1 mM UDP-N-acetylglucosamine or treated with buffer alone (HBSS, 0.1% human serum albumin) for 1 hour at 37° C. After the incubation, the cells are washed with HBSS containing 0.2% BSA and 20 mM HEPES.

Western blot analysis: Untreated and FTVI treated MSC were lysed using 2% NP-40 in Buffer A (150 mM NaCl, 50 mM Tris-HCl, pH 7.4, 1 mM EDTA, 20 μg/ml PMSF, 0.02% sodium azide; and protease inhibitor cocktail tablet (Roche Molecular Biochemicals)). Western blots of quantified protein lysates or of immunoprecipitated protein were performed under reducing conditions as described previously (10).

Immunoprecipitation studies: Cell lysates of untreated or FTVI treated MSC were incubated with immunoprecipitating antibodies or with appropriate isotype controls and then incubated with Protein G-agarose. Immunoprecipitates were washed extensively using Buffer A containing 2% NP-40, 1% SDS. In some experiments, immunoprecipitates were treated with N-glycosidase F (New England Biolabs) as previously described (10, 12)). For Western blot analysis, all immunoprecipitates were diluted in reducing sample buffer, boiled, then subjected to SDS-PAGE, transferred to PVDF membrane, and immunostained with HECA-452, E-Ig, SACK-1 or 2C5 (10).

Parallel plate flow chamber adhesion assay: E-selectin binding capacity of untreated and FTVI-treated MSC was evaluated using a parallel plate flow chamber (Glycotech; Gaithersburg, Md.). MSC ($0.5 \times 10^6$ cells/ml, suspended in HBSS/10 mM HEPES/2 mM $CaCl_2$ solution) were drawn over confluent HUVEC monolayers. Initially, the MSC were allowed to contact the HUVEC monolayer at a shear stress of 0.5 dyne/$cm^2$, subsequently the flow rate was adjusted to exert shear stress ranging from 0.5 to 30 dynes/$cm^2$. The number of untreated or FTVI-treated MSC adherent to the HUVEC monolayer was quantified in the final 15 sec interval at shear stress of 0.5, 1, 2, 5, 10, 20 and 30 dyne/$cm^2$. Each assay was performed at least 3 times and the values averaged. Control assays were performed by adding 5 mM EDTA to the assay buffer to chelate $Ca^{2+}$ required for selectin binding or treating HUVEC with function-blocking anti-human E-selectin mAb (68-5411) at 37° C. for 15 min. prior to use in adhesion assays.

In vivo homing: All studies were performed in accordance with NIH guidelines for the care and use of animals and under approval of the Institutional Animal Care and Use Committees of the Massachusetts General Hospital and the Harvard Medical School. For intravital microscopy, NOD/SCID mice were anesthetized and a small incision was made in the scalp to expose the underline dorsal skull surface as previously described (5). Experiments were performed on the same day using littermates to analyze each of four groups of MSC (n=4 for each group): (1) FTVI treated (as above) MSC; (2) Buffer-treated MSC; (3) FTVI-treated MSC digested with sialidase (100 MU/ml V. Cholera Sialidase, 37° C., 1 hour); and (4) untreated MSC. Cells were stained with the fluorescent lipophilic tracer dye DiD (10 μM, 37° C., 30 min; Molecular Probes) and infused into tail vein of NOD/SCID mice. The interactions of MSC with bone marrow microvascular endothelial cells within the parasagittal region were monitored and imaged at different time points after injection by in vivo confocal microscopy using progressive scanning and optical sectioning combined with video-rate imaging as previously described (5). For delineation of bone marrow vasculature, long-circulating fluorescent quantum dots (Qtracker 800, Invitrogen) were injected systemically just prior to imaging. Stock solution of Qtracker 800 (2 µM) was diluted 1:4 (50 µL mixed in 150 µL PBS 1×) and injected into anesthetized mouse via tail vein. In vivo confocal microscopy of the mouse skull bone marrow was performed as previously described (5). DiD-labeled cells were excited with a solid-state 633 nm laser and imaged with a 45 nm bandpass filter centered at 695 nm, while quantum dots were excited with a solid-state Nd:YAG laser at 532 nm and imaged with a 770 nm longpass filter.

Example 2

Human Mesenchymal Stem Cells Express N-Linked, Sialylated Glycoforms of CD44 and do not Bind Selectins Bone marrow contains two populations of stem cells, hematopoietic stem cells and mesenchymal stem cells (MSC). MSC represent a small population of cells present within normal marrow, but they can be isolated and expanded in culture. MSC characteristically express CD44 and several other adhesion molecules found on hematopoietic cells (14). However, it is unknown whether these primitive non-hematopoietic cells express any selectin ligands. This paucity of data, and the finding that HCELL is expressed among only the earliest hematopoietic cells (CD34+/lin– cells) (10, 11), prompted us to examine whether MSC display similar carbohydrate modifications on CD44 that could bind selectins.

Figure 1:
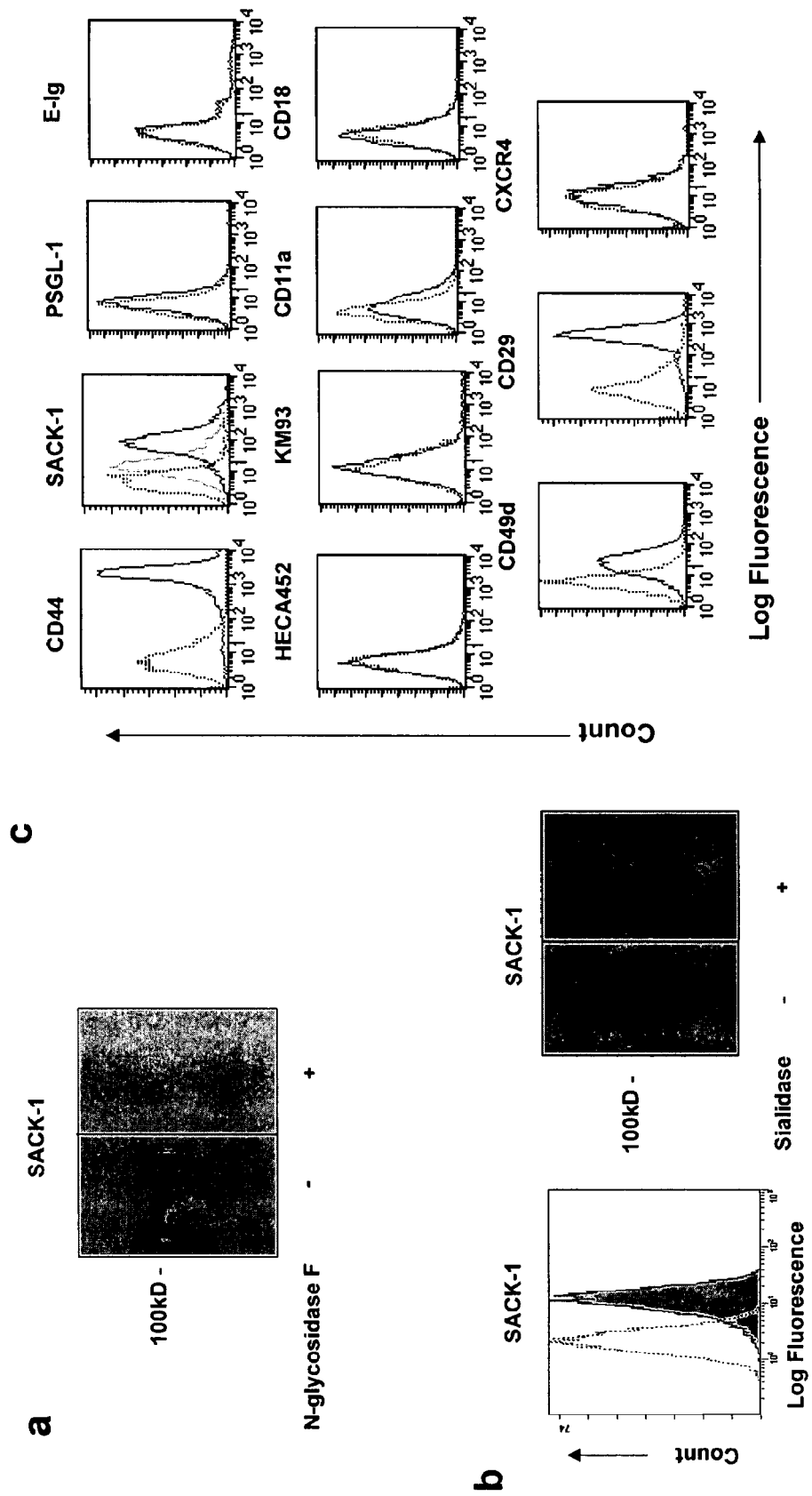
FIG. 1. Human mesenchymal stem cells (MSC) express CD44 and react with SACK-1 mAb, which recognizes a sialic acid-dependent epitope displayed on an N-glycan substitution exclusively carried on a CD44 scaffold. (a) SACK-1 staining of Western blots of untreated (−) or N-Glycosidase-F-treated (+) immunoprecipitated CD44 from KG1a cells (a human cell line that natively expresses HCELL) resolved on a reducing 4-20% SDS-PAGE gel. (b) (Left panel) Flow cytometry analysis of SACK-1 expression on untreated (gray histogram) or sialidase treated (white histogram) KG1a cells. (Right panel) SACK-1 staining of Western blots of untreated (−) or sialidase-treated (+) immunoprecipitated CD44 from KG1a cells resolved on reducing 4-20% SDS-PAGE gel. SACK-1 reactivity is markedly diminished following sialidase treatment, as shown by both flow cytometry and Western blot. (c) Flow cytometry analysis of E-selectin ligand activity (E-selectin-Ig chimera (E-Ig) binding) and of PSGL-1, CD44, SACK-1, HECA452, KM93 (sLe$^x$), CD11a/CD18 (LFA-1), CD49d/CD29 (VLA-4) and CXCR4 expression on MSC. Dotted line is isotype control, black line is specific antibody (or E-Ig chimera); shaded histogram on SACK-1 profile denotes reactivity following sialidase treatment of MSC. Results shown are representative of multiple histograms from MSC derived from multiple marrow donors. Note that human MSC express CD44 and a CD44 glycoform displaying SACK-1 determinants, but do not express E-selectin ligands (no staining with E-selectin-Ig chimera); they also lack CXCR4 and PSGL-1, and also lack the sLe$^x$ determinants recognized by KM93 and HECA452 mAbs.

MSC were cultured from human bone marrow as per two established, published protocols (15, 16). The MSC derived using both methods were capable of multipotential differentiation toward adipocyte, osteocyte and fibroblast differentiation, as previously described (15, 16). Regardless of protocol, MSC displayed no significant differences in any of the measured cell surface markers or in their response to enzymatic treatments. By flow cytometry (FIG. 1c), MSC lacked expression of PSGL-1 or of sialofucosylated determinants that could serve as selectin ligand(s): notably, the cells were devoid of reactivity to mAb KM93 or HECA452 (each of which identify sialyl Lewis X) and to E-Ig by both flow cytometry and Western blot (FIGS. 1c, 2a and 2b). Additionally, both types of MSC lacked LFA-1 (CD11a/CD18) but expressed another integrin, VLA-4 (CD49d/CD29) (FIG. 1c). VLA-4 can mediate rolling interactions and firm adherence on vascular endothelium (17), but both of these adhesive functions require "inside-out" activation usually mediated by the SDF-1/CXCR4 pathway (18). Importantly, analysis of immunofluoresence staining on adherent MSC on plates and by flow cytometry showed no expression of CXCR4 (FIG. 1c) and, predictably, MSC did not migrate in response to SDF-1 in either static or flow-based assays (not shown).

CD44 expression was high among all MSC isolated from numerous donors (FIG. 1c). Conspicuously, SACK-1 reactivity was also high on all MSC from all donors (FIG. 1c), indicating that these cells uniformly expressed N-linked, sialylated glycoforms of CD44. The native absence of selectin ligands but presence of a sialylated CD44 acceptor made MSC an ideal cell type to examine how HCELL expression affects cellular trafficking to bone marrow.

Example 3

Ex Vivo Fucosylation of Mesenchymal Stem Cells Results in HCELL Expression

Figure 2:
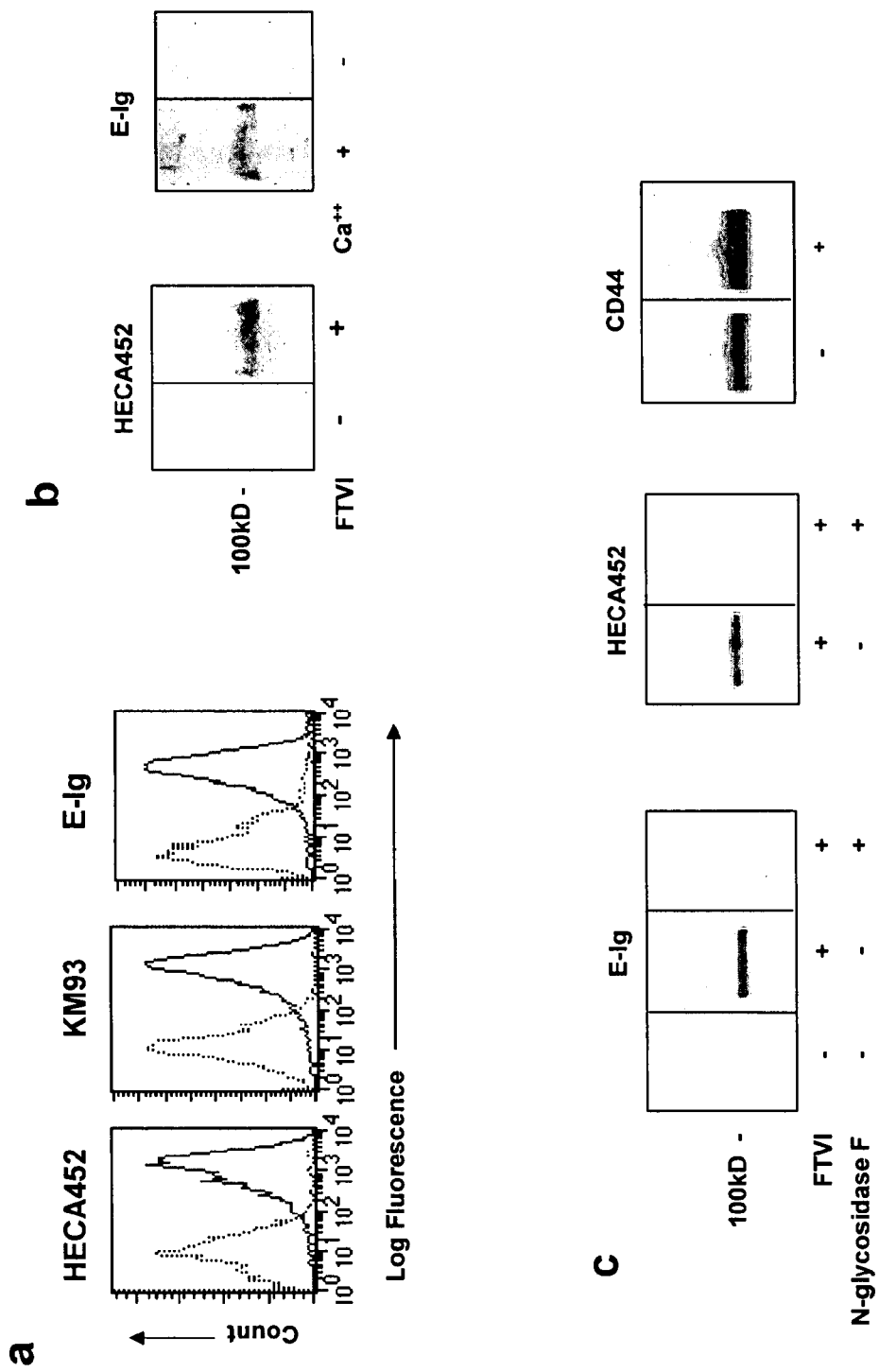
FIG. 2. FTVI treatment of human MSC elaborates sialofucosylations on N-linked glycans of CD44 rendering HCELL expression. (a) Flow cytometry analysis of HECA452, KM93 (sLe$^x$) and E-Ig reactivity on untreated and FTVI-treated MSC. Dotted line is untreated MSC, black line is FTVI-treated MSC. (b) Western blot analysis of HECA452 (left panel) and of E-Ig (right panel) reactivity of MSC lysates resolved on a reducing 4-20% SDS-PAGE. Amounts of lysates in each lane are normalized for cell number of untreated and FTVI-treated MSC. Staining with E-Ig was performed in the presence (+) or absence (−) of $Ca^{2+}$. Note that FTVI treatment induces HECA452-reactive sialofucosylations and E-Ig binding selectively on a ~100 kDa glycoprotein. (c) MSC were treated (+) or untreated (−) with FTVI.

To enforce HCELL expression, MSC were treated ex vivo with an α(1,3)-fucosyltransferase, fucosyltransferase VI (FTVI). In all MSC cultured from all donors, forced fucosylation resulted in profound staining with mAb HECA452 and KM93, consistent with expression of sialyl Lewis X epitopes (FIG. 2a). Western blot of cell lysates and of immunoprecipitated CD44 from FTVI-treated MSC revealed that the only glycoprotein bearing requisite sialofucosylations recognized by HECA452 was CD44 (FIGS. 2b and 2c). Moreover, fucosylated MSC bound E-Ig by flow cytometry, and Western blot analysis of cell lysates showed that the only glycoprotein supporting E-Ig binding was CD44 (FIG. 2). The relevant sialofucosylations of HCELL were displayed on N-glycans, as shown by abrogation of E-Ig binding following digestion with N-glycosidase F (FIG. 2c).

To analyze the E-selectin ligand activity of FTVI-treated MSC under physiologic blood flow conditions, parallel plate flow chamber studies were performed using human umbilical vein endothelial cells (HUVEC) stimulated by cytokines to express E-selectin. As shown in FIG. 3, FTVI-treated MSC showed profound E-selectin ligand activity, which was completely abrogated in the presence of EDTA and by treatment of MSC with sialidase. Consistent with prior studies of cells natively expressing HCELL, robust shear-resistant interactions were observed within usual post-capillary venular shear levels (1-4 dynes/cm$^2$), and persisted at upwards of 20 dyne/cm$^2$, well outside the range where PSGL-1 can support E-selectin binding (10). These data indicated that the HCELL created by fucosylation of MSC surfaces was functionally similar to that displayed natively on the surface of KG1a cells and human hematopoietic progenitor cells (10, 11).

Example 4

HCELL Expression Conferred Enhanced Homing of MSC to Bone Marrow In Vivo

To determine whether HCELL expression conferred enhanced homing of MSC to bone marrow in vivo, we employed dynamic real-time confocal microscopy to visualize marrow sinusoidal vessels in the calvarium of live immunodeficient mouse (NOD/SCID) hosts (5). Four groups of cells were injected into tail vein of respective hosts: (1) FTVI-treated MSC, (2) FTVI-treated MSC digested with sialidase ("FTVI-Sialidase MSC"), (3) buffer-treated MSC, and (4) untreated MSC. In vivo microscopy studies showed that FTVI-treated, HCELL-expressing MSC rolled directly on marrow sinusoidal vessels, and infiltrated the marrow parenchyma rapidly, within hours of infusion (FIG. 4,). In contrast, untreated MSC and buffer-treated MSC showed minimal binding interactions with sinusoidal endothelium and displayed only modest infiltrates, whereas FTVI-Sialidase MSC typically showed even lower levels of endothelial interactions and marrow infiltrates (FIG. 4,). The latter finding highlights the critical role of HCELL in homing, and also indicates that the marrow tropism following FTVI treatment was not a result of fucosylation per se or of indirect effects on other adhesion molecules, but is a consequence solely of the induced selectin ligand activity, requiring concomitant expression of α(2,3)-sialic acid and α(1,3)-fucose modifications. Images obtained with simultaneous staining of MSC and blood vessels clearly show that HCELL+MSC infiltrated the marrow parenchyma (FIG. 4). The observed marrow infiltrates are striking given that studies herein were performed without injury induction, such as by use of radiation or other preparative manipulations of recipient animals that markedly augment expression of sinusoidal ligands promoting marrow trafficking (27). Collectively, these data provide definitive evidence that HCELL expression directly enhances homing of MSC to bone marrow.

In the canonical multi-step paradigm, homing receptor-mediated rolling interactions on the endothelium facilitates exposure to chemokines presumed critical for G-protein-coupled upregulation of integrin adhesiveness with resulting firm adhesion followed by transmigration (3). Notably, the MSC used here did not bear CXCR4 or undergo chemotaxis to SDF-1, the principal chemokine regulating bone marrow homing (4, 5). Thus, the capacity of these cells to infiltrate marrow shows that CXCR4 engagement is not compulsory for marrow trafficking. However, Step 1 interactions are indispensable for cell trafficking to any tissue, and, as shown here, augmentation of E-selectin ligand activity promotes marrow homing. Viewed more broadly, our findings are consistent with a growing body of experimental evidence indicating that engagement of homing receptors may be sufficient alone (i.e., absent chemokine signaling) to induce integrin adhesiveness, with accompanying firm adherence and trans-endothelial migration (1). Notably, it has been found that ligation of CD44 itself on lymphocytes results in direct, synergistic upregulation of VLA-4 adhesiveness, leading to transmigration without chemokine involvement (28). Though future studies will be needed to determine whether this axis operates in other cell types, the fact that MSC characteristically express VLA-4 (FIG. 1c) raises this possibility.

Example 5

In Vivo Fucosylation of Neural Stem Cells

Neural stem cells were treated with 60 mU/mL of FT-VI, 1 mM GDP-fucose or treated with buffer alone (HBSS, 0.1% human serum albumin) for 1 hour at 37° C. Cells were lysed in a buffer containing 2% NP-40. Proteins were separated on a 4-20% Tris-HCl gradient gel in denaturing conditions and transferred to a PVDF membrane. Membrane was immunoblotted with HECA452 antibody. Resulting blot shows the expression of HECA452 reactive epitopes on a number of proteins after forced fucosylation. FT-VI-treated neural stem cells were also analyzed for HECA452 reactivity using flow cytometry. FT-VI-Cells were incubated with 10 ug/mL of HECA452 or 10 ug/mL Rat IgM isotype control for 30 min at 4° C. and subsequently with 20 ug/mL of anti-Rat IgM-FITC for 30 min at 4° C. The flow cytometric results show an increase in HECA452 epitope expression on the cell surface after enforced fucosylation.

Example 6

In Vivo Fucosylation of Pulmonary Stem Cells

Pulmonary stem cells were treated with 60 mU/mL of FT-VI, 1 mM GDP-fucose or treated with buffer alone (HBSS, 0.1% human serum albumin) for 1 hour at 37° C. Cells were incubated with 10 ug/mL of HECA452 or 10 ug/mL Rat IgM isotype control for 30 min at 4° C. and subsequently with 20 ug/mL of anti-Rat IgM-FITC for 30 min at 4° C. The flow cytometric results show an increase in HECA452 epitope expression on the cell surface after forced fucosylation.

REFERENCES

1. R. Sackstein, *Curr Opin Hematol* 12, 444 (2005).
2. T. Lapidot, A. Dar, O. Kollet, *Blood* 106, 1901 (2005).
3. T. A. Springer, *Cell* 76, 301 (1994).
4. A. Peled et al., *Science* 283, 845 (1999).
5. D. A. Sipkins et al., *Nature* 435, 969 (2005).
6. M. J. Polley et al., *Proc Natl Acad Sci USA* 88, 6224 (1991).
7. K. M. Schweitzer et al., *Am J Pathol* 148, 165 (1996).
8. P. S. Frenette, S. Subbarao, I. B. Mazo, U. H. von Andrian, D. D. Wagner, *Proc Natl Acad Sci USA* 95, 14423 (1998).
9. Z. Laszik et al., *Blood* 88, 3010 (1996).
10. C. J. Dimitroff, J. Y. Lee, S. Rafii, R. C. Fuhlbrigge, R. Sackstein, *J Cell Biol* 153, 1277 (2001).
11. C. J. Dimitroff, J. Y. Lee, R. C. Fuhlbrigge, R. Sackstein, *Proc Natl Acad Sci U S A* 97, 13841 (2000).
12. R. Sackstein, C. J. Dimitroff, *Blood* 96, 2765 (2000).
13. C. J. Dimitroff, J. Y. Lee, K. S. Schor, B. M. Sandmaier, R. Sackstein, *J Biol Chem* 276, 47623 (2001).
14. M. F. Pittenger, B. J. Martin, *Circ Res* 95, 9 (2004).
15. M. F. Pittenger et al., *Science* 284, 143 (1999).
16. G. D'Ippolito et al., *J Cell Sci* 117, 2971 (2004).
17. R. Alon et al., *J Cell Biol* 128, 1243 (1995).
18. V. Grabovsky et al., *J Exp Med* 192, 495 (2000).
19. B. W. Murray, S. Takayama, J. Schultz, C. H. Wong, *Biochemistry* 35, 11183 (1996).
20. N. Schrantz et al., *Cell Death Differ* 6, 445 (1999).
21. K. M. de Bruyn, S. Rangarajan, K. A. Reedquist, C. G. Figdor, J. L. Bos, *J Biol Chem* 277, 29468 (2002).
22. A. Chigaev et al., *J Biol Chem* 276, 48670 (2001).
23. Y. Takamatsu, P. J. Simmons, J. P. Levesque, *Cell Adhes Commun* 5, 349 (1998).
24. M. M. Kobzdej, A. Leppanen, V. Ramachandran, R. D. Cummings, R. P. McEver, *Blood* 100, 4485 (2002).
25. L. Xia, J. M. McDaniel, T. Yago, A. Doeden, R. P. McEver, *Blood* 104, 3091 (2004).
26. A. Hidalgo, P. S. Frenette, *Blood* 105, 567 (2005).
27. I. B. Mazo, E. J. Quackenbush, J. B. Lowe, U. H. von Andrian, *Blood* 99, 4182 (2002).
28. A. Nandi, P. Estess, M. Siegelman, *Immunity* 20, 455 (2004).
29. L. Yao et al., *Blood* 94, 3820 (1999).
30. J. Mocco et al., *Circ Res* 91, 907 (2002).

A number of embodiments of the invention have been described. Nevertheless, it will be understood that various modifications may be made without departing from the spirit and scope of the invention. Accordingly, other embodiments are within the scope of the following claims.

What is claimed is:

1. A method of modifying CD44 expressed on the surface of a population of CD44-expressing cells comprising treating the population of cells in vitro with
   a purified α-1,3-fucosyltransferase capable of transferring 1.0 μmole of fucose to an acceptor per minute at pH 6.5 at 37° C. without the input of divalent metal co-factors and a fucose donor in a physiologically acceptable solution without the input of divalent metal co-factors,
   thereby forming a population of modified cells wherein the CD44 structures on the surfaces of the population of modified CD44-expressing cells bind E-selectin, and wherein the population of modified CD44-expressing cells has a viability of at least 70% at 24 hours after the treatment.

2. The method of claim 1, wherein said CD44-expressing cells modified without the input of divalent metal co-factors are CD34⁻ prior to said treatment.

3. The method of claim 1, wherein said CD44-expressing cells modified without the input of divalent metal co-factors are CD34⁺ prior to said treatment.

4. The method of claim 1, wherein said population of CD44-expressing cells modified without the input of divalent metal co-factors is a population of stem cells or a population of differentiated cells.

5. The method of claim 1, wherein said population of CD44-expressing cells modified without the input of divalent metal co-factors is a hematopoietic stem cell population, a mesenchymal stem cell population, a tissue stem/progenitor cell population, an umbilical cord stem cell population, or an embryonic stem cell population.

6. The method of claim 5, wherein said population of CD44-expressing cells modified without the input of divalent metal co-factors is a tissue stem/progenitor cell population and the tissue stem/progenitor cell population is modified without the input of divalent metal co-factors selected from a neural stem cell population, a myocyte stem cell population, or a pulmonary stem cell population.

7. The method of claim 1, wherein said population of CD44-expressing cells modified without the input of divalent metal co-factors bind L-selectin.

8. The method of claim 1, wherein said population of CD44-expressing cells modified without the input of divalent metal co-factors do not bind P-selectin.

9. The method of claim 4, wherein said population of differentiated CD44-expressing cells is a lymphocyte or leukocyte cell population.

10. The method of claim 1, wherein the viability of the modified CD44-expressing cell population is at least 80% at 12 hours after contact with the α-1,3-fucosyltransferase.

11. The method of claim 1, wherein the viability of the modified CD44-expressing cell population is at least 80% at 24 hours after contact with the α-1,3-fucosyltransferase.

12. The method of claim 1, wherein the viability of the modified CD44-expressing cell population is at least 90% at 12 hours after contact with the α-1,3-fucosyltransferase.

13. The method of claim 1, wherein the viability of the modified CD44-expressing cell population is at least 90% at 24 hours after contact with the α-1,3-fucosyltransferase.

14. A method of modifying CD44 expressed on the surfaces of a population of CD44-expressing cells, the method comprising treating the population of cells ex vivo with
   i) a purified sialyltransferase in a physiologically acceptable solution without the input of divalent metal co-factors and in the presence of a sialic acid donor; and
   ii) a purified α-1,3-fucosyltransferase capable of transferring 1.0 μmole of fucose to an acceptor per minute at pH 6.5 at 37° C. without the input of divalent metal co-factors and a fucose donor in a physiologically acceptable solution without the input of divalent metal co-factors;
thereby forming a population of CD44-expressing cells modified without the input of divalent metal co-factors, wherein the modified CD44-expressing cells have fucosylated CD44 structures on the surfaces thereof and bind E-selectin, and wherein the population has a viability of at least 70% at 24 hours after the treatment.

15. The method of claim 14, wherein said CD44-expressing cells modified without the input of divalent metal co-factors are CD34⁻ prior to said treatment.

16. The method of claim 14, wherein said CD44-expressing cells modified without the input of divalent metal co-factors are CD34⁺ prior to said treatment.

17. The method of claim 14, wherein said CD44 expressed on the surface of cells of said cell population is non-sialylated prior to modification without the input of divalent metal co-factors.

18. The method of claim 14, wherein said population of CD44-expressing cells modified without the input of divalent metal co-factors is a population of differentiated cells or a population of stem/progenitor cells.

19. The method of claim 18, wherein said population of CD44-expressing cells modified without the input of divalent metal co-factors is a hematopoietic stem cell population, a mesenchymal stem cell population, a tissue stem/progenitor cell population, an umbilical cord stem cell population, or an embryonic stem cell population.

20. The method of claim 19, wherein said population of CD44-expressing cells modified without the input of divalent metal co-factors is a tissue stem/progenitor cell population and the tissue stem/progenitor cell population is a neural stem cell population, a myocyte stem cell population or a pulmonary stem cell population.

21. The method of claim 14, wherein said population of cells modified without the input of divalent metal co-factors bind L-selectin.

22. The method of claim 14, wherein said population of CD44-expressing cells modified without the input of divalent metal co-factors do not bind P-selectin.

23. The method of claim 19, wherein said population of differentiated CD44-expressing cells modified without the input of divalent metal co-factors and expressing CD44 is a lymphocyte or leukocyte cell population.

24. The method of claim 14, wherein the viability of the modified CD44-expressing cell population is at least 80% at 12 hours after contact with the α-1,3-fucosyltransferase.

25. The method of claim 14, wherein the viability of the modified CD44-expressing cell population is at least 80% at 24 hours after contact with the α-1,3-fucosyltransferase.

26. The method of claim 14, wherein the viability of the modified CD44-expressing cell population is at least 90% at 12 hours after contact with the α-1,3-fucosyltransferase.

27. The method of claim 14, wherein the viability of the modified CD44-expressing cell population is at least 90% at 24 hours after contact with the α-1,3-fucosyltransferase.

* * * * *